US00PP24212P2

(12) United States Plant Patent
van der Meer

(10) Patent No.: US PP24,212 P2
(45) Date of Patent: Feb. 4, 2014

(54) *CHRYSANTHEMUM* PLANT NAMED 'BKGARDPU'

(50) Latin Name: *Chrysanthemum×morifolium*
Varietal Denomination: Bkgardpu

(75) Inventor: Adrianus L. M. van der Meer, Monster (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 13/507,244

(22) Filed: Jun. 14, 2012

(51) Int. Cl.
*A01H 5/00* (2006.01)

(52) U.S. Cl.
USPC ..... Plt./287

(58) Field of Classification Search
USPC ..... Plt./287
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Bkgardpu', characterized by its compact, upright and mounded plant habit; dark green-colored leaves; uniform and early flowering response; freely flowering habit; decorative-type inflorescences with dark red purple-colored ray florets; and good garden performance.

2 Drawing Sheets

Botanical designation: *Chrysanthemum×morifolium.*
Cultivar denomination: 'BKGARDPU'.

BACKGROUND OF THE INVENTION

The present invention relates to a new and distinct cultivar of *Chrysanthemum* plant, botanically known as *Chrysanthemum×morifolium*, commercially grown as a Garden *Chrysanthemum* plant and hereinafter referred to by the name 'Bkgardpu'.

The new *Chrysanthemum* plant is a naturally-occurring whole plant mutation of the *Chrysanthemum×morifolium* 'Bkgardrs', not patented. The new *Chrysanthemum* plant was discovered by the Inventor in October, 2010 as a single flowering plant from within a population of plants of 'Bkgardrs' in a controlled greenhouse environment in Monster, The Netherlands.

Asexual reproduction of the new *Chrysanthemum* plant by vegetative tip cuttings was first conducted in Maasdijk, The Netherlands in January, 2011. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural practices. The phenotype may vary somewhat with variations in environment such as temperature, daylength and light intensity, without, however, any variance in genotype.

The following traits have been repeatedly observed and are determined to be the unique characteristics of 'Bkgardpu'. These characteristics in combination distinguish 'Bkgardpu' as a new and distinct garden *Chrysanthemum* plant:

1. Compact, upright and mounded plant habit.
2. Dark green-colored foliage.
3. Uniform flowering response.
4. Early flowering habit, eight-week response time.

5. Freely flowering habit.
6. Decorative-type inflorescences with dark red purple-colored ray florets.
7. Good garden performance.

Plants of the new *Chrysanthemum* differ from plants of the parent, 'Bkgardrs', primarily in ray floret coloration as plants of the new *Chrysanthemum* have red purple-colored ray florets whereas plants of 'Bkgardrs' have pink-colored ray florets.

Plants of the new *Chrysanthemum* can be compared to plants of *Chrysanthemum* 'Daphin Purple', not patented. In side-by-side comparisons conducted in Monster, The Netherlands, plants of the new *Chrysanthemum* differed from plants of 'Daphin Purple' in the following characteristics:

1. Plants of the new *Chrysanthemum* were more compact than plants of 'Daphin Purple'.
2. Plants of the new *Chrysanthemum* had larger leaves than plants of 'Daphin Purple'.
3. Plants of the new *Chrysanthemum* had larger inflorescences than plants of 'Daphin Purple'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of typical flowering plant of 'Bkgardpu' grown in a container.

The photograph on the second sheet is a close-up view of the upper (top of sheet) and lower (bottom of sheet) surfaces of typical inflorescences and leaves of 'Bkgardpu'.

DETAILED BOTANICAL DESCRIPTION

The aforementioned photographs and following observations and measurements describe plants grown in 12-cm containers during the spring in a glass-covered greenhouse in Monster, The Netherlands and under cultural practices which approximate those generally used in commercial garden *Chrysanthemum* production. During the production of the plants, day and night temperatures ranged from about 18° C. to 19° C. Plants were grown under photoinductive short day/long night treatments, not pinched and were two months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Bkgardpu'.

Parentage: Naturally-occurring whole plant mutation of the *Chrysanthemum×morifolium* 'Bkgardrs', not patented.

Propagation:

*Type.*—Terminal vegetative cuttings.

*Time to initiate roots, summer.*—About ten days at temperatures of about 18° C. to 19° C.

*Time to initiate roots, winter.*—About twelve days at temperatures of about 18° C. to 19° C.

*Time to produce a rooted young plant, summer.*—About 14 days at temperatures of about 18° C. to 19° C.

*Time to produce a rooted young plant, winter.*—About 16 days at temperatures of about 18° C. to 19° C.

*Root description.*—Medium in thickness, fibrous; white in color.

*Rooting habit.*—Freely branching; medium density.

Plant description:

*Plant and growth habit.*—Herbaceous garden type *Chrysanthemum* with decorative-type inflorescences; compact and bushy plant habit; stems initially upright and arching outwardly giving a uniformly mounded appearance; overall plant form, obovate to flattened obovate; moderately vigorous growth habit; freely branching habit with about twelve lateral branches developing per plant.

*Plant height.*—About 16.8 cm.

*Plant width.*—About 15.8 cm.

*Lateral branches.*—Length: About 6.2 cm. Diameter: About 2.5 mm. Internode length: About 1.2 cm. Strength: Strong. Texture: Densely pubescent. Color: Close to 143C.

Foliage description:

*Arrangement.*—Alternate, simple.

*Length.*—About 5 cm.

*Width.*—About 4.5 cm.

*Shape.*—Broadly ovate, palmately lobed.

*Apex.*—Acute.

*Base.*—Attenuate.

*Margin.*—Palmately lobed, sinuses between lateral lobes slightly convergent.

*Texture, upper surface.*—Pubescent.

*Texture, lower surface.*—Densely pubescent; veins prominent.

*Color.*—Developing leaves, upper surface: Close to 143A. Developing leaves, lower surface: Close to 138B. Fully expanded leaves, upper surface: Close to N137D; venation, close to 146B. Fully expanded leaves, lower surface: Close to 147B; venation, close to 146B.

*Petiole length.*—About 1 cm.

*Petiole diameter.*—About 2 mm.

*Petiole texture, upper and lower surfaces.*—Densely pubescent.

*Petiole color, upper and lower surfaces.*—Close to 146B.

Inflorescence description:

*Appearance.*—Decorative-type inflorescence form with obovate to oblong-shaped ray florets; inflorescences borne on terminals above the foliar plane; disc and ray florets arranged acropetally on the capitulum.

*Fragrance.*—Moderately fragrant.

*Flowering response.*—Under natural season conditions, plants flower in the autumn in the Netherlands; under controlled greenhouse environment conditions, inflorescence initiation and development can be induced under short day/long night conditions (at least 13.5 hours of darkness); early flowering habit; plants flower about eight weeks after planting.

*Postproduction longevity.*—Inflorescences maintain good color and substance for about three weeks; inflorescences not persistent.

*Quantity of inflorescences.*—Freely flowering habit with about 50 inflorescences developing per plant.

*Inflorescence buds.*—Height: About 5 mm. Diameter: About 7 mm. Shape: Flattened globular. Color: Close to 143A and 143D.

*Inflorescences.*—Diameter: About 4 cm. Depth (height): About 2 cm. Diameter of disc: About 4 mm. Receptacle diameter: About 3 mm. Receptacle height: About 2 mm. Receptacle color: Close to 145B.

*Ray florets.*—Orientation: Initially upright, then about 30° to 60° from perpendicular to peduncle. Number of ray florets per inflorescence: About 170 arranged in about seven whorls. Length: About 1.5 cm. Width: About 6 mm. Shape: Obovate to oblong. Apex: Emarginate. Base: Cuneate. Margin: Entire. Texture, upper and lower surfaces: Smooth, glabrous, velvety; longitudinally ridged. Color: When opening, upper surface: Between 64A and 71A. When opening, lower surface: Close to N78D. Fully opened, upper surface: Close to 71A to 71B; color does not fade with development. Fully opened, lower surface: Close to 75A.

*Disc florets.*—Arrangement: Massed at center of receptacle. Number of disc florets per inflorescence: About 15. Shape: Tubular, elongated. Apex: Five-pointed, acute. Length: About 5 mm. Width: About 1.5 mm. Color, immature: Apex: Close to 13A. Mid-section and base: Close to 145C to 145D. Color, mature: Apex: Close to 12A and 13A. Mid-section and base: Close to 145C.

*Phyllaries.*—Number of phyllaries per inflorescence: About 20 arranged in about three whorls. Length: About 7 mm. Width: About 2.5 mm. Shape: Narrowly ovate to oblong. Apex: Bluntly acute. Base: Cuneate. Texture, upper surface: Smooth, glabrous. Texture, lower surface: Pubescent. Color, upper surface: Close to 143A; margins, close to N199A. Color, lower surface: Close to 143A to 143B; margins, close to N199A.

*Peduncles.*—Length: First peduncle: About 3.1 cm. Fourth peduncle: About 4.8 cm. Diameter (first peduncle): About 2 mm. Angle: Erect to about 30° from vertical. Strength: Strong, flexible. Texture: Densely pubescent. Color: Close to 138B.

*Reproductive organs.*—Androecium: Present on disc florets only. Quantity of stamens per disc floret: About five. Filament length: About 1 mm. Filament color: Close to 145B to 145C. Anther shape: Narrowly oblong. Anther length: About 1.2 mm. Anther color: Close to 154D. Pollen amount: Moderate. Pollen color: Close to 6A. Gynoecium: Present on both ray and disc florets. Quantity of pistils per floret: One. Pistil length: About 4 mm. Stigma shape: Cleft, decurrent. Stigma color: Close to 9A to 9B. Style length: About 3.5 mm. Style color: Close to 145B to 145C. Ovary color: Close to 144B to 144C.

*Seeds and fruits.*—Seed and fruit production has not been observed on plants of the new *Chrysanthemum.*

Disease & pest resistance: Resistance to pathogens and pests common to *Chrysanthemum* plants has not been observed on plants of the new *Chrysanthemum* grown under commercial conditions.

Garden performance: Plants of the new *Chrysanthemum* have been observed to have good garden performance, to tolerate high temperatures of about 35° C. and to be hardy to USDA Hardiness Zones 7 to 8.

It is claimed:

1. A new and distinct *Chrysanthemum* plant named 'Bkgardpu' as illustrated and described.

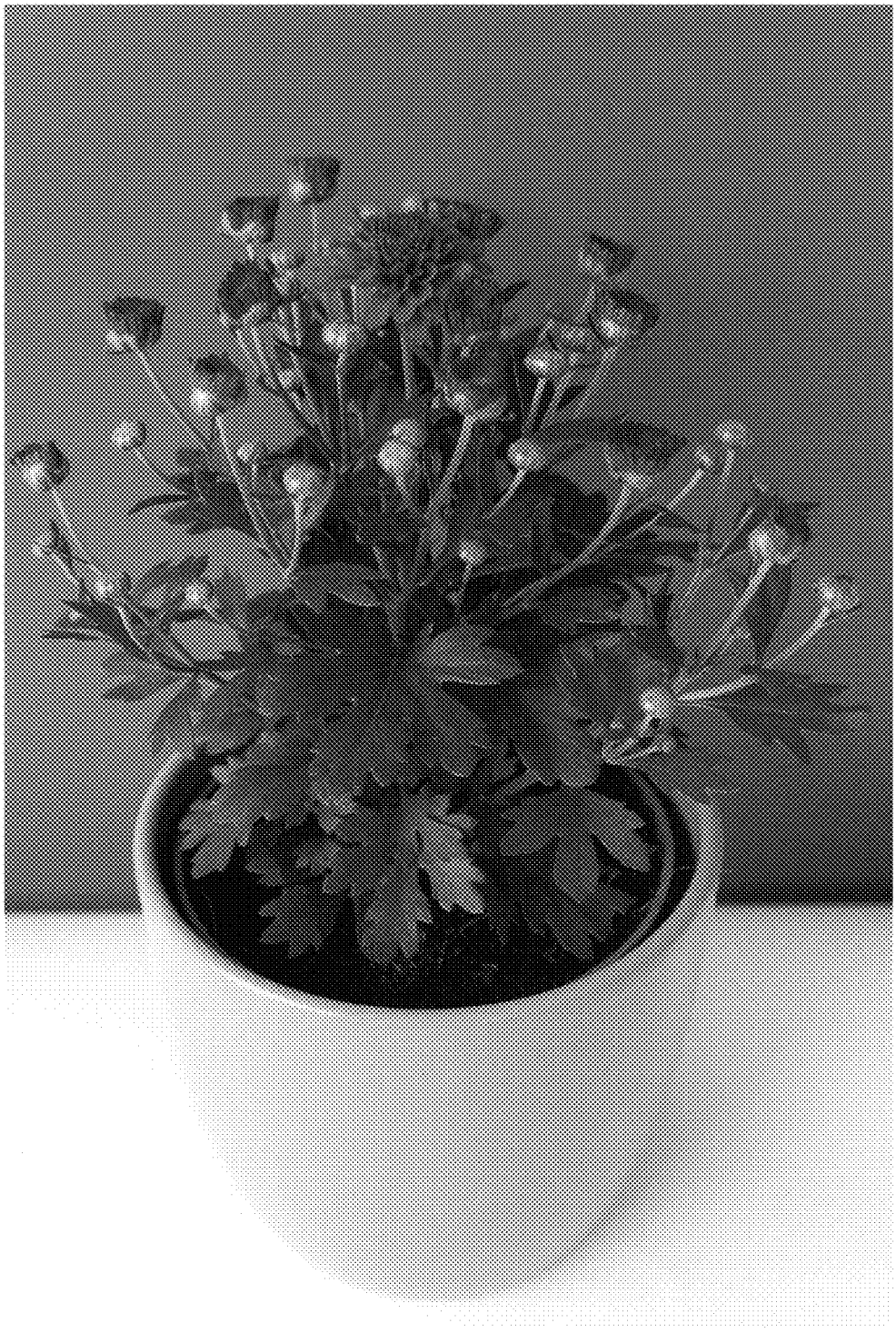

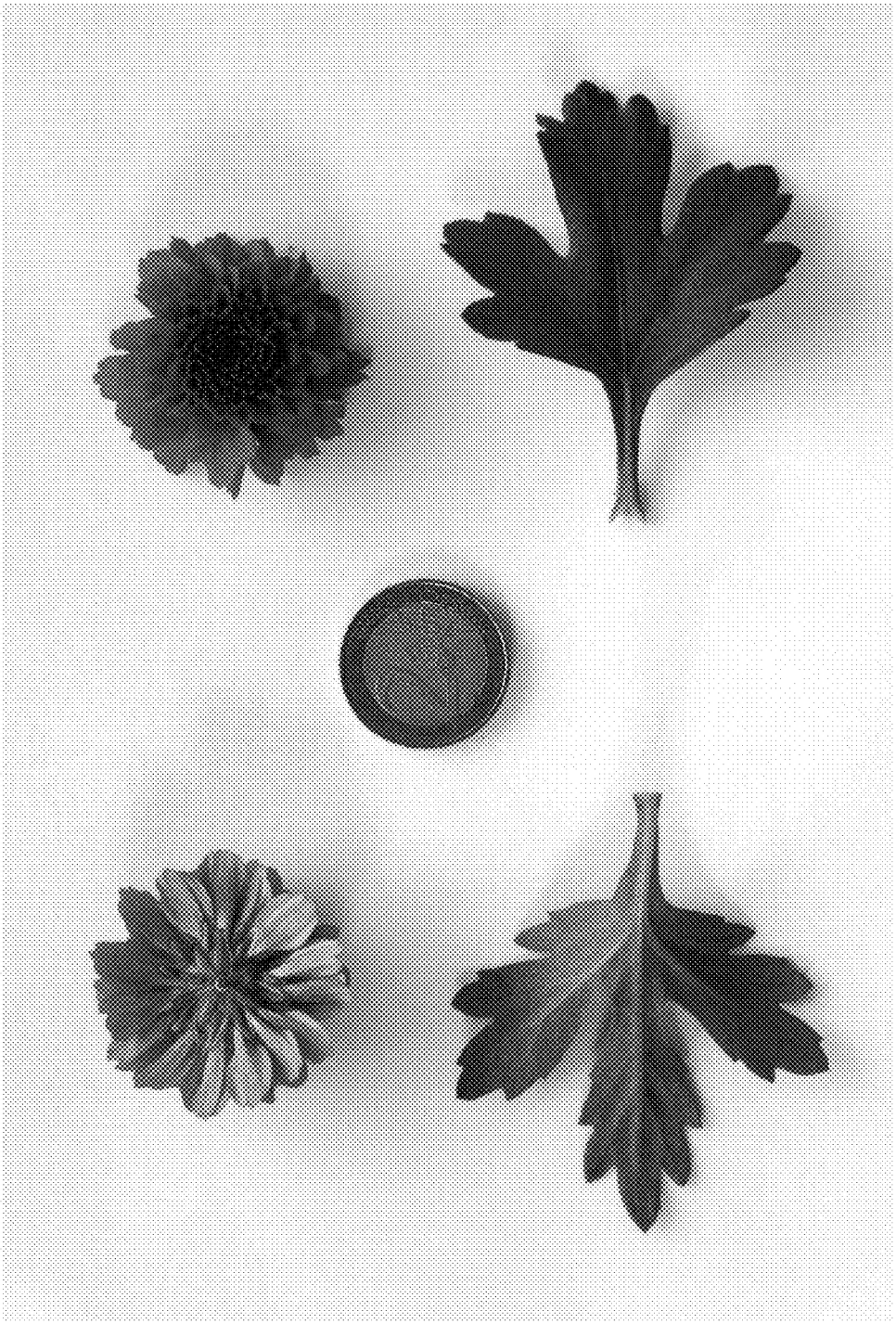

* * * * *